United States Patent [19]

Mabilat et al.

[11] Patent Number: 5,786,147
[45] Date of Patent: Jul. 28, 1998

[54] DETECTION OF ENTEROBACTERIA

[75] Inventors: Claude Mabilat, Rillieux la Pape; Raoult Didier, Marseilles, both of France

[73] Assignee: Bio Merieux, Marcy L'Etoile, France

[21] Appl. No.: 717,526

[22] Filed: Sep. 17, 1996

[30] Foreign Application Priority Data

Sep. 24, 1995 [FR] France ................... 95 11125

[51] Int. Cl.⁶ .................. C12Q 1/68; C07H 21/02
[52] U.S. Cl. .................................. 435/6; 536/23.1
[58] Field of Search .................... 435/6; 439/91.2; 536/23.1; 935/77, 78

[56] References Cited

FOREIGN PATENT DOCUMENTS

| | | |
|---|---|---|
| 0 473 268 A2 | 3/1992 | European Pat. Off. . |
| 0 578 962 A2 | 1/1994 | European Pat. Off. . |
| WO 93/222454 | 11/1993 | WIPO . |
| WO 93/22454 | 11/1993 | WIPO . |
| WO 94/24565 | 10/1994 | WIPO . |

OTHER PUBLICATIONS

A. Lazcano et al., "On the Early Evolution of RNA Polymerase", *Journal of Molecular Evolution*, vol. 27, pp. 365–376 (1988).

L. Post et al., "Nucleotide Sequence of the Ribosomal Protein Gene Cluster Adjacent to the Gene, for RNA Polymerase Subunit β in *Escherichia coli*", *Proc. Natl. Acad. Sci. U.S.A.*, vol. 76, No. 4, pp. 1697–1701 (1979).

J. Olsen et al., "Rearrangements in Unintegrated Retroviral DNA Are Complex and Are the Result of Multiple Genetic Determinants", *Journal of Virology*, vol. 64, No. 11, pp. 5475–5484 (1990).

R. Cibotti et al., "Public and Private Vβ T Cell Receptor Repertoires Against Hen Egg White Lysozyme (HEL) in Nontransgenic Versus HEL Transgenic Mice", *J. Exp. Med.*, vol. 180, pp. 861–870 (1994).

*Primary Examiner*—Eggerton A. Campbell
*Attorney, Agent, or Firm*—Oliff & Berridge PLC

[57] ABSTRACT

The invention relates to a single-stranded oligonucleotide chosen from oligonucleotides having a sequence of at least 12 consecutive nucleotide units which is included in one of the sequences SEQ ID NO: 1 to SEQ ID NO: 52, and from the oligonucleotides complementary to these oligonucleotides, and to the applications of this oligonucleotide for detecting enterobacteria.

32 Claims, 9 Drawing Sheets

FIG. 1

|  | 1 | 11 | 21 | 31 | 41 | 51 |
|---|---|---|---|---|---|---|
| Escherichia coli | ********* | GCAGCAGTGA | AAGAGTTCTT | CGGTTCCAGC | CAGCTGTCTC | AGTTTATGGA |
| Shigella dysenteriae | --------- | ---------- | ---------- | ---------- | ---------- | ---------- |
| Kluyvera ascorbata | --------- | ---------- | ---------- | ---------- | ---------- | ---------- |
| Escherichia fergussoni | --------- | ---------- | ---------- | T--------- | ---------- | ---------- |
| Enterobacter cloacae | --------- | ---------- | ---------- | T--------- | ---------- | -----C---- |
| Klebsiella pneumoniae ODC | --------- | --G------- | ---------- | T--------- | ---------- | ---------- |
| Salmonella sofia | --------- | --G------- | ---------- | T--------- | ---------- | ---------- |
| Salmonella typhimurium | --------- | --C------- | ---------- | T--------- | ---------- | ---------- |
| Pseudomonas putida | GCCGGTAGCG | ------G--- | ---------- | --CA------ | -------C-- | -----C---- |
| Mycobacterium tuberculosis | --------- | --C--GA-C- | --G------- | --CA------ | ----AGC--- | ---------- |
| Mycobacterium leprae | --------- | --C--TA-C- | --G--A---- | --CA------ | -------G-- | -A---C---- |
| Bacillus subtilis | --------- | --GT-CA-T- | ---------- | T--AAG-TCA | -----T---- | ---------- |
| Buchnera aphidicola | --------- | --T--TA-T- | ---A--T--- | T-----T--- | --AT-A--G- | -A---C---- |
| Thermotoga maritima | --------- | T--A-G--C- | ---CC----- | --CGATG-A- | -----T---- | -----C---- |
| Thermoplasma acidophilum | --------- | T*****--GC | -CTG-A-AGG | ---CAGA-CG | GGCG-A--G- | ---C-AC--- |
| Thermococcus celer | --------- | --GA-G-GTT | CGTG-CC-GG | T--CAGA-C- | GGTG-G--AGC | ---C-GC--- |
| Sulfolobus acidocaldarius | --------- | ---A---GA- | -CTG-G-TGG | ---AGA-CT | GGAG-AAG-- | -A--AC-A-- |

FIG. 2

| | 61 | 71 | 81 | 91 | 101 | 111 |
|---|---|---|---|---|---|---|
| Escherichia coli | CCAGAACAAC | CCGCTGTCTG | AGATTACGCA | CAAACGTCGT | ATCTCCGCAC | TCGGCCCAGG |
| Shigella dysenteriae | ---------- | -------C-- | ---------- | ---------- | ---------- | ---------- |
| Kluyvera ascorbata | ---------- | ---------- | ---------- | ---------- | ---------- | -----G---- |
| Escherichia fergussoni | ---------- | ---------- | -------A-- | ---------- | ---------- | ---------- |
| Enterobacter cloacae | ---------- | ---------- | ---------- | ----G----- | ---------- | ---------- |
| Klebsiella pneumoniae ODC | ---------- | ---------- | ---------- | ---------- | -----T---- | ---------- |
| Salmonella sofia | ---------- | ---------- | ---------- | ---------- | ---------- | ---------- |
| Salmonella typhimurium | ---------- | ---------- | ---------- | ---------- | ---------- | ---------- |
| Pseudomonas putida | ---------- | ---T--C--G | ---------C | ---G--C--C | --TG------ | --------T- |
| Mycobacterium tuberculosis | ---------- | ------G--- | G-T-G--C-- | ---G--C--A | C-G--G--G- | ---G--G--C |
| Mycobacterium leprae | ---------- | ---T-----G | GCC-G--C-- | ---G--C--G | C-G--G--G- | ---G---G-- |
| Bacillus subtilis | T-----CG-- | -----TG--- | -AT-A----- | ---G------ | C-G--A---T | --A--A--G- |
| Buchnera aphidicola | T--A-T--T | --AT-A--A- | -A-------A | T---A-AA-A | --T-A---T | -G-A-TT-- |
| Thermotoga maritima | T---GTG-T- | ---T-----G | -AC-C--T-- | ----A-AA-G | G-T-T--TG | ----A-C-- |
| Thermoplasma acidophilum | -AG-GTTTC- | AAC--CAGCA | C---C--GC- | TCTGA-GA-G | -AATT-G- | CTCTTA--A- |
| Thermococcus celer | -AG--CG--- | TACA-A--GA | C-C-CT-C- | -CTCA-G--C | G--A--T-G- | CGCT-AGCA- |
| Sulfolobus acidocaldarius | TAGA-CA--T | TG---A--CA | T-T-A-GT- | TCTTA-GA-A | G-AGTTT--T | CTTTAG-CA- |

FIG. 3

| | 121 | 131 | 141 | 151 | 161 | 171 |
|---|---|---|---|---|---|---|
| Escherichia coli | CGGTCTGACC | CGTGAACGTG | CAGGCTTCGA | AGTTCGAGAC | GTACACCCGA | CTCACTACGG |
| Shigella dysenteriae | ---------- | ---------- | ---------- | ---------- | ---------- | ---------- |
| Kluyvera ascorbata | ---------- | ---------- | ---------- | ---------- | ---------- | ---------- |
| Escherichia fergussoni | ---------- | --------C- | ---------- | ---------- | ---------- | ---------- |
| Enterobacter cloacae | ---------- | ----G--C-- | ---------- | ---------- | ---------- | -C-------- |
| Klebsiella pneumoniae ODC | ---------- | ----G--C-- | ---------- | ---------- | ---------- | -G-------- |
| Salmonella sofia | ---------- | ---C------ | ---------- | ---------- | ---------- | -G-------- |
| Salmonella typhimurium | ---------- | ---C---TG- | ---------- | ---------- | ---------- | -G-------- |
| Pseudomonas putida | ---------- | -------G-- | ---C------ | --C--T---- | ---------- | -C-------- |
| Mycobacterium tuberculosis | ----T--A-- | -------G-- | -C--GC-G-- | G--C--C--- | --G------T | -G-------- |
| Mycobacterium leprae | T---T--T-G | -------G-- | -C--GC-A-- | G--C--T--- | --G----TT | -G-------- |
| Bacillus subtilis | --AT----A- | -------G-- | -C--AA-G-- | ---G--T--- | --T---TACT | -C--T----- |
| Buchnera aphidicola | T---T-A--T | A-A----A-A | ----A----- | ---A----T | ---T--A--- | ----T--T-- |
| Thermotoga maritima | T--AT---GA | A-A---TCCA | A--T------ | --CAA--A-- | --G---TACT | ---G------ |
| Thermoplasma acidophilum | GACG-A-C-- | -ACTTCGAG- | --A-GGA-CT | TCA--CGAC- | CAGTGGGGA- | GGATA-G-CC |
| Thermococcus celer | G-AA-A-C-G | -A-TTCGAG- | -CC-TGA-CT | TCACG--AC- | CACTGGGGC- | GGATA-GTCC |
| Sulfolobus acidocaldarius | G--A-A-C-T | AA-TTTGAG- | -GA-AGA-CT | TCA-G--ACT | CA-TGGGA- | GAATG-G-CC |

FIG. 4

| Organism | 181 | 191 | 201 | 211 | 221 | 231 |
|---|---|---|---|---|---|---|
| Escherichia coli | TCGCGTATGT | CCAATCGAAA | CCCCTGAAGG | TCCGAACATC | GGTCTGATCA | ACTCTCTGTC |
| Shigella dysenteriae | ---------- | ---------- | ---------- | ---------- | ---------- | ---------- |
| Kluyvera ascorbata | ---------- | ---------- | -G-------- | ---A------ | ---------- | ----C----- |
| Escherichia fergussoni | ---------- | ---------- | ---------- | ---------- | ---------- | ---------- |
| Enterobacter cloacae | ---------- | ---------- | -G-------- | ---A------ | ---------- | ----C----- |
| Klebsiella pneumoniae ODC | ---------- | --G------- | -G-------- | ---------- | ---------- | ----C----- |
| Salmonella sofia | ---------- | ---------- | -G--G----- | ---------- | -------T-- | ----C----- |
| Salmonella typhimurium | ---------- | --T------- | -G--G----- | ---------- | ---------- | ----C----- |
| Pseudomonas putida | C--T--G--C | -G-------G | ---------- | ---------- | ---------- | ----C---G- |
| Mycobacterium tuberculosis | C--GA-G--C | -G-------- | --------G- | G--C------ | ---------G | G--G------ |
| Mycobacterium leprae | C--GA-G--C | -G------G- | -T--G--G-- | C-------A  | --------G  | GT--AT---- |
| Bacillus subtilis | C--TA-G--- | -G--T----- | -G--G----- | C--------- | ------T--- | ----A--A-- |
| Buchnera aphidicola | A--T--C--- | -T--A----- | -A--A----- | G--A-T--T  | --AT----T  | -T---T-A-- |
| Thermotoga maritima | AA-GC-G--- | -C--T----- | -A--C----- | CG------A  | -AT-C--A-  | CA-------G |
| Thermoplasma acidophilum | CAA--A-AC- | --GAG-G-C  | AGAACTGC-- | --T-GT--AG | AACGCCGC-C | T-CTCA-AAA |
| Thermococcus celer | GAC--AGACC | --CGAG-GTC | -GAACTGC-- | --TCGT--AG | AAC--CGC-C | T-ATGTCCCA |
| Sulfolobus acidocaldarius | GTTT-A-ACA | --TGAA-GTC | -TAACAGT-- | A-TTGTG-AA | AA---AGC-T | TG-TAGCACA |

FIG. 5

| | 241 | 251 | 261 | 271 | 281 | 291 |
|---|---|---|---|---|---|---|
| Escherichia coli | CGTGTACGCA | CAGACTAACG | AATACGGCTT | CCTTGAGACT | CCGTATCGTA | AAGTGACCGA |
| Shigella dysenteriae | ---------- | ---------- | ---------- | ---------- | ---------- | ---------- |
| Kluyvera ascorbata | ---------- | ---------- | ---------- | ---------- | ----C----- | ---------- |
| Escherichia fergussoni | ---------- | ---------- | -----T---- | ---------- | ----C----- | -----TT--- |
| Enterobacter cloacae | ---------- | ----A----- | ---------- | -------G-- | ---------- | ------T--- |
| Klebsiella pneumoniae ODC | ---------- | ----C----- | -----T---- | -------C-- | ---------- | ---------- |
| Salmonella sofia | -------G-- | ---------- | ---------- | -------G-- | ---------- | -------A-- |
| Salmonella typhimurium | ---------- | ---------- | -----T---- | -------G-- | -----C---- | ---GT---GTT |
| Pseudomonas putida | ---------- | ---------- | ---------- | -------G-- | -----C---- | ---GT---GTT |
| Mycobacterium tuberculosis | G-CC-T--C | -GC--C---C | -G-------- | --G-A-GC-- | -----C--CG | TG------AG- |
| Mycobacterium leprae | G-------- | -G-GTC---C | CG-T----G- | -A-C--A--G | -----C---- | ---G----GT- |
| Bacillus subtilis | G-------- | -G-GTC---C | CC-T----G- | -A-C--A--A | -----C---- | ---G----GTT |
| Buchnera aphidicola | ATCT--T-- | A-AGTA---C | GT-TT----- | TA---A--G | --A-----CC | GC--TGA-CC |
| Thermotoga maritima | A----T--T | -GA----TT | C---T--A- | TT-A--A--A | --T-----A- | -G--ACATA- |
| Thermoplasma acidophilum | TA-A----T | A-A-TCG-T- | --------A- | T--CAT---- | --T--A-A-- | -G--AGT-A- |
| Thermococcus celer | ---ACGCAG | GGC-TCG-TC | CTG--A--G- | -A-G-----TA | -T-A-GG-G- | TG-ACGT-CG |
| Sulfolobus acidocaldarius | GA-AAC-A-C | GG-GT-CCA- | -GG-G-AGG- | -AGG--ATAC | -T-G-GA-AC | TC-GAGT--T |
| | G--T-CT-TT | GGT-T----- | -G-CA-TAG- | -GAGAG-GTA | G-T---GAAT | T--GAGT--T |

FIG. 6

| | 301 | 311 | 321 | 331 | 341 | 351 |
|---|---|---|---|---|---|---|
| Escherichia coli | CGGTGTTGTA | ACTGACGAAA | TTCACTACCT | GTCTGCTATC | GAAGAAGGCA | ACTACGTTAT |
| Shigella dysenteriae | ---------- | ---------- | ---------- | ---------- | ---------- | ---------- |
| Kluyvera ascorbata | ---------- | ---C------ | ----T----- | ---------- | ---------- | ---------- |
| Escherichia fergussoni | ---------- | ---C------ | ---------- | ---------- | ---------- | ---------- |
| Enterobacter cloacae | -------T-- | ---C------ | ----T----- | ---------T | ---------- | ---------- |
| Klebsiella pneumoniae ODC | ----G--T-- | ---------- | ---------- | ---------- | ---------- | ---------- |
| Salmonella sofia | T--C--G--C | ---------- | ----T----- | ---------- | ---------- | ---------- |
| Salmonella typhimurium | T--C--G--T | ---------- | ----T----- | ---------- | ---------- | ---------- |
| Pseudomonas putida | A--C------ | ---------C | -CGTG-T--- | ---G--A--- | ------*--- | GA-CACG-CA |
| Mycobacterium tuberculosis | ---C--G--T | -GC-----G- | -CGTG----- | -A-C--CGA- | --G--G-A-C | G-C-----GG |
| Mycobacterium leprae | ---G--C--- | -GC-----G- | -CG-A----T | -A-C---GA- | --G----A-C | G-C-T---CG |
| Bacillus subtilis | T-AAACA-GG | -AG-TAACGG | GCAGAAT-GA | T-ACTTA-CT | -CT--T-AAG | -GG-TAACTA |
| Buchnera aphidicola | -C--T-A--- | -----T---- | -A----TT-- | A-----A--A | ----G--A-- | -T-------- |
| Thermotoga maritima | T--AAAA--- | --G--T--G | -GGT---T-- | -AGG--C-A- | ------AAG | -G---AAA-- |
| Thermoplasma acidophilum | --AG--CC-G | GAG--GAGCC | CGA-GA-AGG | -CG--T-TAT | CTGA-T--AG | -T-T-A-AGG |
| Thermococcus celer | TCCGA-A-AG | GAGAGGAG-C | CAA--CC-GA | CCTCTGGCG- | CTCT-CCTT- | --GG----C- |
| Sulfolobus acidocaldarius | GA----A-A- | GA--TAAT-- | GGAGAAT-AG | TGAGCAA-A- | -----C-TGG | -AA-ATA--- |

FIG. 7

| Species | 361 | 371 | 381 | 391 | 401 | 411 |
|---|---|---|---|---|---|---|
| Escherichia coli | CGCCCAGGCG | AACTCCAACT | TGGATGAAGA | AGGCCACTTC | GTAGAAGACC | TGGTAACTTG |
| Shigella dysenteriae | ---------- | ---------- | ---------- | ---------- | ---------- | ---------- |
| Kluyvera ascorbata | ---T------ | ---------C | ---------- | ---------- | ---------- | ---------- |
| Escherichia fergussoni | ---------- | ---------- | ---------C | ---------T | ---------- | ---------- |
| Enterobacter cloacae | ---------- | ---------- | ---------C | ---------T | ---------- | ---------- |
| Klebsiella pneumoniae ODC | ---T------ | ---------- | ---------C | ---------- | ---------T | ------T--C |
| Salmonella sofia | ---T------ | ---------- | --------A- | ---------- | ---------- | ------T--C |
| Salmonella typhimurium | ---T------ | ---------- | ---------C | C--------- | ---------T | ------T--C |
| Pseudomonas putida | ---T------ | ---------- | ---------C | ---------T | ---------- | ------G--C |
| Mycobacterium tuberculosis | TCG-ACA-GC | TT-GG-CG-G | AT--ACG-C- | --AAGCAACT | -ATCG-TGAG | CT-GT-GCA- |
| Mycobacterium leprae | G--A-----C | --T--GCCGA | -C-----CG- | C--T-G---- | --C--GCCG- | GC--GCTGGT |
| Bacillus subtilis | G--G-----C | ----GCCGA | -C--C--G-C | C----GT-C- | TCGAGCCG-G | C-TGTTGGGT |
| Buchnera aphidicola | T-TTGTC--T | C-AG-G--TG | CTCG-CTT-- | T-A-G-AGG- | -CCTTTATTG | AT-AC-GCAT |
| Thermotoga maritima | T--A--A--A | --TA-T--TA | -A----A--A | TAATT----T | A-T--T-TT | -A-----C-- |
| Thermoplasma acidophilum | -ATA-CT--C | --C-A-ACC-G | ---------- | G---A--A-A | A--CC---GA | GA---GTGGC |
| Thermococcus celer | ATAT--C-AT | G-TC-G-GA- | ACCT--TTTC | GA-GATACG- | -AG--GCG-A | G-TC-GGCC- |
| Sulfolobus acidocaldarius | --TTGGAA-C | GTGGAGG-TG | G---G-GCTT | C-TGA--AGA | A--CG-AC-G | ACAGG-GAA- |
| | GAGTTG-AGT | --GGTTT--C | -TA---GTAG | -TTATTAGGA | TATT-C--GG | AT-GT-AAGA |

FIG. 8

| | 421 | 431 | 441 | 451 | 461 | 471 |
|---|---|---|---|---|---|---|
| Escherichia coli | CCGTAGCAAA | GGCGAATCCA | GCTTGTTCAG | CCGCGACCAG | GTTGACTACA | TGGACGTATC |
| Shigella dysenteriae | ---------- | ---------- | ---------- | ---------- | ---------- | ---------- |
| Kluyvera ascorbata | ---------- | ---------- | ---------- | ---------- | ---------- | ---------- |
| Escherichia fergussoni | ---------- | ---------- | ---------- | ---------- | ---------- | ---------- |
| Enterobacter cloacae | ---------- | ---------- | ---------- | ---------- | ---------- | ---------- |
| Klebsiella pneumoniae ODC | ---------- | ---------- | ---------- | ---------- | ---------- | ---------- |
| Salmonella sofia | ---------- | ---------- | ---------- | ---T------ | ---------- | ---------- |
| Salmonella typhimurium | ---------- | ---------- | ---------- | ---------- | ---------- | ----T----- |
| Pseudomonas putida | TTCGTCACCT | -AACG-ATTC | A-CGTCAAG- | -GC--GAAGA | CG-C--CCTG | AT-GACGT-T |
| Mycobacterium tuberculosis | --CC----G | -CG-GCGAGG | TGGA--A-GT | G-C-TCGTCT | -AG-TGG--T | ACATG-ACGT |
| Mycobacterium leprae | G--CC----G | -CG-GCGAGG | TGGA--A-GT | GGC-TCGTCC | -AG-TGG-TT | ACATG-ATGT |
| Bacillus subtilis | -GTAGCTCGT | TT-CGCGGGG | AGAACAC-GT | TGTTTC-AGA | AA-CGTGTAG | ACT--A-GGA |
| Buchnera aphidicola | TA-GCA--- | --A----T- | -T--A--T-A | -T-TA-T--A | --C--T--- | ---------- |
| Thermotoga maritima | T--A-TGGGT | -AA--TAT-- | -GC-TG-TCC | -AAA--AG-A | --A--T-T-- | ----T----- |
| Thermoplasma acidophilum | -ATGTCGG-T | -AG-T-AA-G | T-AG--ATGA | TGA-A--AC- | --A--T-T-- | ---------- |
| Thermococcus celer | -G-G-AG-T- | A----CAT-- | TAAACG-TGC | --T-T----- | AAC--GGTT | ---------- |
| Sulfolobus acidocaldarius | GTTAGCT--G | AAGATT | | | -A- | |

FIG. 9

```
                                 481        491        501        511        521        531
Escherichia coli              CACCCAGCAG GTGGTATCCG TCGGTGCCGTC CCTGATCCCG TT
Shigella dysenteriae          ---------- ---------- ---------- ---------- --
Kluyvera ascorbata            ---------- ---------- ---------- ---------- --
Escherichia fergussoni        ---------- ---------- ---------- ---------- --
Enterobacter cloacae          ---------- ---------- ---------- ---------- --
Klebsiella pneumoniae ODC     ---------- ----C----- ---------- ---------- --
Salmonella sofia              ---------- ---------- ---------- ---------- --
Salmonella typhimurium        ---------- ----C----- ---------- ---------- --
Pseudomonas putida            -G--G-AGCA -GTTGT-T-C GTT-CAGCGT -GCTGATT-C G-T
Mycobacterium tuberculosis    -T-G-CC-GC CA-A-GGTGT CG-TG--CA- -GC---GATT CCCTT
Mycobacterium leprae          -T-G-CA-GC CA-A-GGTGT CG-TG--CA- AGC---GATT CCGTT
Bacillus subtilis             TGTATC--CT AA-CAGGTT- -ATC----TG- GACAGCATGT A-CCCGTT
Buchnera aphidicola           T--T--A--A A-T----T- -A--A--T-- TT-A--T--A --
Thermotoga maritima           G---GA----A CCCT-CAGT- --TCG--T-- A--C--T--- --
Thermoplasma acidophilum
Thermococcus celer
Sulfolobus acidocaldarius
```

DETECTION OF ENTEROBACTERIA

FIELD OF THE INVENTION

The present invention belongs to the field of detection and/or amplification techniques using oligonucleotide probes or primers, and to their application in testing for the presence of bacteria of the genus Enterobacteriaceae or in identifying these bacteria.

BACKGROUND

In the context of certain diagnostic tests, in particular when testing for septicemic infection or in the food field, it is often necessary to obtain a rapid answer regarding the presence of bacteria, especially Gram-negative bacteria, and more precisely entero-bacteria, in a sample. However, the techniques developed at the present time (Gram staining, biochemical identification, etc.) necessitate a prior step of culture, often under very specific conditions (hemoculture, for example), on account of the small proportion of bacterial particles present in the initial sample.

A possible approach lies in the use of the technologies relating to nucleic acid and to genetic material in order to determine whether a gene, a portion of gene or a nucleotide sequence is present in a living organism, a cell extract of this organism or a sample. In view of the fact that any gene or portion of gene is characterized by a specific sequence of nucleotide bases, it is consequently possible to test directly for the presence of all or part of said specific sequence within a sample containing a mixture of polynucleotides.

Different types of methods of detection of nucleic acids are described in the literature. These methods are based on the properties of purine-pyrimidine pairing of the complementary strands of nucleic acids in DNA-DNA, DNA-RNA and RNA-RNA duplexes. This process of pairing takes place through the establishment of hydrogen bonds between the bases adenine-thymine (A-T) and guanine-cytosine (G-C) of double-stranded DNA; adenine-uracil (A-U) base pairs may also form by hydrogen bonding in DNA-RNA or RNA-RNA duplexes. The pairing of nucleic acid strands for determining the presence or absence of a given nucleic acid molecule is commonly referred to as "nucleic acid hybridization" or simply "hybridization".

According to the present invention, new genetic markers have been identified permitting the specific detection of bacteria belonging to the family of enterobacteria in any sample, not necessitating any prior step of bacterial culture. The invention is based on the use of nucleic acid sequences specifically defined in the rpoB gene coding for one of the subunits of the bacterial RNA polymerase.

According to Lazcano et al., 1988, the RNA polymerases are divided into two groups according to their origin, one consisting of the viral RNA- or DNA- dependent polymerases and the other consisting of the DNA-dependent RNA polymerases of eukaryotic or prokaryotic origin (archaebacteria and eubacteria). The eubacterial DNA-dependent RNA polymerases are characterized by a simple and conserved multimeric constitution designated "core enzyme" and symbolized by abb', or "holoenzyme" and symbolized by abb'a' [Burgess et al., J. Biol. Chem. (1969) 244: 6168–6176; Chamberlin, Ann. Rev. Biochem. (1974) 43: 721–775; Yura and Ishihama, Ann. Rev. Genet. (1979) 13: 59–97; Sentenac, CRC—Crit. Rev. Biochem. (1985) 18(1): 31–90]. Many studies have demonstrated the functional role, within the multimeric enzyme complex, of the b subunit of eubacterial RNA polymerase. The archaebacterial and eukaryotic RNA polymerases possess, for their part, a more complex structure which can reach around ten, or even thirty, subunits [Pühler et al.[]Proc. Natl. Acad. Sci. USA (1989) 86: 4569–4573; Sentenac, CRC—Crit. Rev. Biochem. (1985) 18(1): 31–90].

The genes which code for the different subunits of the DNA-dependent RNA polymerase in eubacteria, rpoA, rpoB, rDoC, and rpoD, respectively, for abb'a', are grouped together in different segments comprising genes coding for proteins that constitute ribosomal subunits or for enzymes involved in genome replication and repair [Yura and Yshihama, Ann. Rev. Genet. (1979) 13: 59–97]. Some authors have shown that the nucleic acid sequences of the rpoB and rpoC genes could be used in order to construct phylogenetic trees [Lazcano et al., J. Mol. Evol. (1988) 27: 365–376; Zillig et al., Can. J. Microbiol. (1989) 35: 73–80; Rowland et al., Biochem. Soc. Trans. (1992) 21: 40S] enabling the different phyla and subphyla among the kingdoms of living organisms to be separated. In addition, it has been shown, in eubacteria, that the b subunit constitutes the target molecule of the rifamycins (including rifampicin), the streptovaricins and streptolydigin [Kumar and Chatterji, Biochemistry (1990) 29: 317–322; Kumar et al., Biochemistry (1992) 31: 7519–7526], and that the rpoB gene constitutes the genetic basis of the resistance of the microbes to these antibiotics [Ovchinnikov et al., Mol. Gen. Genet. (1983) 190: 344–348; Lisitsyn et al., Mol. Gen. Genet. (1984) 196: 173–174]. Numerous mutations of the rpoB gene affecting the regulation of the expression and function of the RNA polymerase have thus been described [Landick et al., Genes Dev. (1990) 4: 1623–1636], some of which are linked to mutations conferring the rifampicin-resistant phenotype [Jin and Gross, J. Biol. Chem. (1991) 266: 14478–14485; Jin and Turnbough, J. Mol. Biol. (1994) 236: 72–80]. Determination of the rifampicin resistance of *Mycobacterium tuberculosis* strains by the use of the rpoB gene has formed the subject of several studies (Hunt et al., 1994, Diagn. Microbiol. Infect. Dis., 18, 219–227; Whelen et al., 1995, J. Cli. Microbiol. 33, 556–561; and Patent Application No. WO 93/22454).

Regions which are variable according to the bacterial family, but which are seen to be conserved within the family Enterobacteriaceae, have now been discovered on the DNA coding for the b subunit of bacterial RNA polymerase, thereby enabling the latter bacterial family to be distinguished from other bacterial families. Moreover, minor sequence variations between some enterobacterial species exist in said conserved regions. These results have enabled nucleic acid probes to be designed which are specific either for the enterobacterial family, or for certain particular species.

The prior art consists, in addition, of the following documents: WO-A-94/24565, EP-0,473,268 and Kanellopoulos et al., Journal of Experimental Medicine, vol. 180, 1994, p. 861–872. As mentioned below, these documents describe nucleotide sequences possessing a succession of nucleotide units which is identical to some of the sequences reported in the present invention, but they neither disclose nor suggest their use for detecting enterobacteria.

Thus, the document WO-A-94/24565 relates to the detection of HCV antigens in a sample using antibodies specific for HCV antigens, and describes the sequence identified in that document by SEQ ID NO: 11 described on page 71. This sequence is identified in the present description by SEQ ID NO: 77.

The document EP-0,473,268 teaches a pharmaceutical composition comprising a polypeptide active principle and permitting a progressive release of the active polypeptide. It describes the sequence identified in that document by SEQ ID NO: 19, and in the present description by SEQ ID NO: 78.

The paper by Kanellopoulos et al. relates to a transgenic mouse, and describes, on line 17 of page 866, the sequence which is identified in the present description by SEQ ID NO: 79.

DEFINITIONS

Before the invention is described in greater detail, different terms used in the description and the claims are defined below:

"nucleic acid extracted from bacteria" is understood either to mean the total nucleic acid, or the genomic DNA, or the messenger RNAs, or the DNA obtained from the reverse transcription of the messenger RNAs;

a "nucleotide fragment" or an "oligonucleotide" are two synonymous terms denoting a linked arrangement of nucleotide units which is characterized by the informational sequence of the natural (or, where appropriate, modified) nucleic acids, and which are capable of hybridizing, like the natural nucleic acids, with a complementary or substantially complementary nucleotide fragment under predetermined conditions. The linked arrangement can contain nucleotide units differing in structure from that of the natural nucleic acids. A nucleotide fragment (or oligonucleotide) can contain, for example, up to 100 nucleotide units. It generally contains at least 10, and especially at least 12, nucleotide units, and may be obtained from a natural nucleic acid molecule and/or by genetic recombination and/or by chemical synthesis, a nucleotide unit is derived from a monomer which can be a natural nucleotide of nucleic acid whose constituent components are a sugar, a phosphate group and a nitrogenous base; in DNA the sugar is 2-deoxyribose, in RNA the sugar is ribose; depending on whether the nucleic acid is DNA or RNA, the nitrogenous base is chosen from adenine, guanine, uracil, cytosine and thymine; or alternatively the monomer is a nucleotide modified in at least one of the three constituent components; as an example, the modification can occur either in the bases, with modified bases such as inosine, 5-methyldeoxycytidine, deoxyuridine, 5-(dimethylamino)deoxyuridine, 2,6-diaminopurine, 5-bromodeoxyuridine or any other modified base capable of hybridization, or in the sugar, for example the replacement of at least one deoxyribose by a polyamide [P. E. Nielsen et al., Science, 254, 1497–1500 (1991)], or in the phosphate group, for example its replacement by esters chosen, in particular, from diphosphates, alkyl- and arylphosphonates and phosphorothioates, "informational sequence" is understood to mean any ordered succession of nucleotide type units whose chemical nature and order in a reference direction constitute an item of information analogous to that given by the sequence of natural nucleic acids, "hybridization" is understood to mean the process during which, under suitable conditions, two nucleotide fragments having sufficiently complementary sequences are capable of associating via stable and specific hydrogen bonds to form a double strand. The hybridization conditions are determined by the "stringency", that is to say the severity of the working conditions. The specificity of the hybridization increases as the stringency at which it is performed rises. Stringency is a function, in particular, of the base composition of a probe/target duplex, as well as of the degree of mispairing between two nucleic acids. The stringency may also be a function of the parameters of the hybridization reaction, such as the concentration and type of ionic species present in the hybridization solution, the nature and concentration of denaturing agents and/or the hybridization temperature. The stringency of the conditions under which a hybridization reaction should be carried out depends, in particular, on the probes used. All these data are well known, and the appropriate conditions may be determined, where appropriate, in each case by routine experiments. In general, depending on the length of the probes used, the temperature for the hybridization reaction is between approximately 20° and 65° C., and especially between 35° and 65° C., in a saline solution at a concentration of approximately 0.8 to 1M, a "probe" is a nucleotide fragment comprising, for example, from 10 to 100 nucleotide units, in particular from 12 to 35 nucleotide units, possessing a specificity of hybridization under particular conditions to form a hybridization complex with a target nucleic acid having, in the present case, a nucleotide sequence included either in a messenger RNA, or in a DNA obtained by reverse transcription of said messenger RNA, or in a DNA of which said messenger RNA is the transcription product; a probe may be used for diagnostic purposes (in particular capture or detection probes) or for therapeutic purposes, a "capture probe" is immobilized or capable of being immobilized on a solid support by any suitable means, for example by covalent bonding, by adsorption, or by direct synthesis on a solid support (see, in particular, Patent Application WO 92/10092), a "detection probe" may be labeled by means of a label chosen, for example, from radioactive isotopes, enzymes, especially enzymes capable of acting on a chromogenic, fluorogenic or luminescent substrate (in particular a peroxidase or an alkaline phosphatase), chromophoric chemical compounds, chromogenic, fluorogenic or luminescent compounds, nucleotide base analogs and ligands such as biotin, a "primer" is a probe comprising, for example, from 10 to 100 nucleotide units and possessing a specificity of hybridization under particular conditions for the initiation of an enzymatic polymerization, for example in an amplification technique such as PCR (polymerase chain reaction), in a sequencing process, in a method of reverse transcription, and the like.

SUMMARY OF THE INVENTION

A first subject of the present invention is a single-stranded oligonucleotide chosen from oligonucleotides having a sequence of at least 12 consecutive nucleotide units which is included in one of the sequences SEQ ID NO: 1 to SEQ ID NO: 52, and from the oligonucleotides complementary to these oligonucleotides, excluding the oligonucleotides having a sequence chosen from the following sequences: SEQ ID NO: 77, SEQ ID NO: 78 and SEQ ID NO: 79.

Preferred oligonucleotides of the invention are a) those which comprise a nucleotide sequence of at least 12 consecutive nucleotide units which is included in one of the sequences SEQ ID NO: 1 to SEQ ID NO: 4, and their complementary sequences, and b) those which comprise a nucleotide sequence of at least 12 consecutive nucleotide units which is included in:

SEQ ID NO: 5 and containing at least 5 consecutive nucleotide units included in SEQ ID NO: 53, SEQ ID NO: 6 and containing at least 5 consecutive nucleotide units included in SEQ ID NO: 54, SEQ ID NO: 7 and containing at least 5 consecutive nucleotide units included in SEQ ID NO: 55, SEQ ID NO: 8 and containing at least 5 consecutive nucleotide units included in SEQ ID NO: 56, SEQ ID NO: 8 and containing at least 5 consecutive nucleotide units included in SEQ ID NO: 57, SEQ ID NO: 9 and containing at least 5 consecutive nucleotide units included in SEQ ID NO: 58, SEQ ID NO: 10 and containing at least 5 consecutive nucleotide units included in SEQ ID NO: 59, SEQ ID NO: 11 and containing at least 5 consecutive nucleotide units included in SEQ ID NO: 60, SEQ ID NO: 12 and containing at least 5 consecutive nucleotide units included in SEQ ID NO: 61, SEQ ID NO: 13 and containing at least 5 consecutive nucleotide units included in SEQ ID NO: 62, SEQ ID NO: 14 and containing at least 5 consecutive nucleotide units included in SEQ ID NO: 63, SEQ ID NO: 15 and containing at least 5 consecutive nucleotide units included in SEQ ID NO: 64, SEQ ID NO: 16 and containing at least 5 consecutive nucleotide units included in SEQ ID NO: 65, SEQ ID NO: 17 and containing at least 5 consecutive nucleotide units included in SEQ ID NO: 64, SEQ ID NO: 18 and containing at least 5 consecutive nucleotide units included in SEQ ID NO: 66, SEQ ID NO: 19 and containing at least 5 consecutive nucleotide units included in SEQ ID NO: 67, SEQ ID NO: 20 and containing at least 5 consecutive nucleotide units included in SEQ ID NO: 68, SEQ ID NO: 21 and containing at least 5 consecutive nucleotide units included in SEQ ID NO: 69, SEQ ID NO: 22 and containing at least 5 consecutive nucleotide units included in SEQ ID NO: 70, SEQ ID NO: 23 and containing at least 5 consecutive nucleotide units included in SEQ ID NO: 71, SEQ ID NO: 24 and containing at least 5 consecutive nucleotide units included in SEQ ID NO: 72, SEQ ID NO: 25 and containing at least 5 consecutive nucleotide units included in SEQ ID NO: 73, SEQ ID NO: 26 and containing at least 5 consecutive nucleotide units included in SEQ ID NO: 74, SEQ ID NO: 27 and containing at least 5 consecutive nucleotide units included in SEQ ID NO: 75, SEQ ID NO: 28 and containing at least 5 consecutive nucleotide units included in SEQ ID NO: 76, or which comprise a complementary sequence.

Preferred oligonucleotides b) comprise or consist of a nucleotide sequence chosen from the sequences SEQ ID NO: 29 to SEQ ID NO: 52.

A second subject of the invention is a probe for the detection, in a biological sample, of bacteria belonging to the family of enterobacteria, said probe consisting of an oligonucleotide of the invention according to a). In the description which follows, such a probe of the invention will be referred to as a genus probe.

A third subject of the invention is a probe for the detection, in a biological sample, of at least one species of enterobacteria, said probe consisting of an oligonucleotide of the invention according to b). Such probes of the invention will be referred to in the present description as species probes.

The probes according to the invention may be used for diagnostic purposes in testing for the presence or absence of a target nucleic acid in a sample, according to all known hybridization techniques, and in particular the techniques of application as a dot to a filter, termed "dot-blot" (Maniatis et al., Molecular Cloning, Cold Spring Harbor, 1982), the DNA transfer techniques termed "Southern blot" [Southern, E. M., J. Mol. Biol., 98, 503 (1975)], the RNA transfer techniques termed "northern blot", or the so-called "sandwich" techniques [Dunn A. R., Hassel J.A., Cell, 12, 23 (1977)]; the sandwich technique is used especially, with a capture probe and/or a detection probe, said probes being capable of hybridizing with two different regions of the target nucleic acid, and at least one of said probes (generally the detection probe) being capable of hybridizing with a region of the target which is specific to the species or group of species being tested for, on the understanding that the capture probe and the detection probe must have nucleotide sequences which are at least partially different.

In order to carry out the abovementioned hybridization techniques, and especially the "sandwich" techniques, a probe of the invention is immobilized on a solid support—this will be the capture probe—and another probe of the invention is labeled with a tracing agent—this will be the detection probe.

The invention relates, in addition, to the uses of an oligonucleotide chosen from oligonucleotides having a sequence of at least 12 consecutive nucleotide units which is included in one of the sequences SEQ ID NO: 1 to SEQ ID NO: 52, and from the oligonucleotides complementary to these oligonucleotides, as a probe and as a primer.

Another subject of the invention is a method for the determination of the presence or absence of at least one enterobacterium in a sample containing or likely to contain nucleic acids of at least one such bacterium, comprising the steps that consist in bringing said sample into contact with at least one oligonucleotide of the invention as used as a genus or species probe, and then in determining in a manner known per se the formation or absence of formation of a hybridization complex between said oligonucleotide and the nucleic acid of the sample.

According to a particular embodiment of this method for the determination of the presence or absence of a species or group of species of enterobacterium, an oligonucleotide as used as a genus probe according to the invention is used on the one hand and an oligonucleotide as used as a species probe according to the invention is used on the other hand, on the understanding that said oligonucleotides are capable of hybridizing with nonoverlapping regions of a nucleic acid corresponding to the rpoB gene of enterobacteria.

Advantageously, the genus probe is immobilized on a solid support and the species probe is labeled with a tracing agent.

The subject of the present invention is also the application of the method of the invention for determining the presence of a particular species of enterobacterium.

Thus, the invention relates to:

a method for the determination of the presence or absence of *Salmonella sofia*, according to which a probe is used chosen from those comprising a nucleotide sequence of at least 12 consecutive nucleotide units which is included in one of the sequences chosen from:

SEQ ID NO: 5 and containing at least 5 consecutive nucleotide units included in SEQ ID NO: 53, SEQ ID NO: 27 and containing at least 5 consecutive nucleotide units included in SEQ ID NO: 75, and their complementary sequences.

Preferably, a probe for the species *Salmonella sofia* has a nucleotide sequence which consists of or which comprises a sequence chosen from SEQ ID NO: 29, SEQ ID NO: 51 and their complementary sequences;

a method for the determination of the presence or absence of *Salmonella typhimurium*, according to which a probe is used chosen from those comprising a nucleotide sequence of at least 12 consecutive nucleotide units which is included in one of the sequences chosen from:

SEQ ID NO: 6 and containing at least 5 consecutive nucleotide units included in SEQ ID NO: 54, SEQ ID NO: 11 and containing at least 5 consecutive nucleotide units included in SEQ ID NO: 60, SEQ ID NO: 24 and containing at least 5 consecutive nucleotide units included in SEQ ID NO: 72, SEQ ID NO: 25 and containing at least 5 consecutive nucleotide units included in SEQ ID NO: 73, and their complementary sequences.

Preferably, a probe for the species *Salmonella typhimurium* has a nucleotide sequence which consists of or which comprises a sequence chosen from SEQ ID NO: 30, SEQ ID NO: 35, SEQ ID NO: 48, SEQ ID NO: 49, SEQ ID NO: 52 and their complementary sequences;

a method for the determination of the presence or absence of *Shigella dysenteriae*, according to which a probe is used chosen from those comprising a nucleotide sequence of at least 12 consecutive nucleotide units which is included in SEQ ID NO: 7 and containing at least 5 consecutive nucleotide units included in SEQ ID NO: 55 and its complementary sequence.

Preferably, a probe for the species *Shigella dysenteriae* has a nucleotide sequence which consists of or which comprises a sequence chosen from SEQ ID NO: 31 and its complementary sequence;

a method for the determination of the presence or absence of *Escherichia fergussoni*, according to which a probe is used chosen from those comprising a nucleotide sequence of at least 12 consecutive nucleotide units which is included in one of the sequences chosen from:

SEQ ID NO: 8 and containing at least 5 consecutive nucleotide units included in SEQ ID NO: 56, SEQ ID NO: 8 and containing at least 5 consecutive nucleotide units included in SEQ ID NO: 57, SEQ ID NO: 19 and containing at least 5 consecutive nucleotide units included in SEQ ID NO: 67, and their complementary sequences.

Preferably, a probe for the species *Escherichia fergussoni* has a nucleotide sequence which consists of or which comprises a sequence chosen from SEQ ID NO: 32, SEQ ID NO: 43 and their complementary sequences;

a method for the determination of the presence or absence of *Enterobacter cloacae*, according to which a probe is used chosen from those comprising a nucleotide sequence of at least 12 consecutive nucleotide units which is included in one of the sequences chosen from:

SEQ ID NO: 9 and containing at least 5 consecutive nucleotide units included in SEQ ID NO: 58, SEQ ID NO: 13 and containing at least 5 consecutive nucleotide units included in SEQ ID NO: 62, SEQ ID NO: 16 and containing at least 5 consecutive nucleotide units included in SEQ ID NO: 65, SEQ ID NO: 17 and containing at least 5 consecutive nucleotide units included in SEQ ID NO: 64, SEQ ID NO: 18 and containing at least 5 consecutive nucleotide units included in SEQ ID NO: 66, SEQ ID NO: 21 and containing at least 5 consecutive nucleotide units included in SEQ ID NO: 69, SEQ ID NO: 22 and containing at least 5 consecutive nucleotide units included in SEQ ID NO: 70, and their complementary sequences.

Preferably, a probe for the species *Enterobacter cloacae* has a nucleotide sequence which consists of or which comprises a sequence chosen from SEQ ID NO: 33, SEQ ID NO: 37, SEQ ID NO: 40, SEQ ID NO: 41, SEQ ID NO: 42, SEQ ID NO: 45, SEQ ID NO: 46 and their complementary sequences;

a method for the determination of the presence or absence of *Klebsiella pneumoniae*, according to which a probe is used chosen from those comprising a nucleotide sequence of at least 12 consecutive nucleotide units which is included in one of the sequences chosen from:

SEQ ID NO: 10 and containing at least 5 consecutive nucleotide units included in SEQ ID NO: 59, SEQ ID NO: 14 and containing at least 5 consecutive nucleotide units included in SEQ ID NO: 63, SEQ ID NO: 15 and containing at least 5 consecutive nucleotide units included in SEQ ID NO: 64, SEQ ID NO: 20 and containing at least 5 consecutive nucleotide units included in SEQ ID NO: 68, SEQ ID NO: 23 and containing at least 5 consecutive nucleotide units included in SEQ ID NO: 71, and their complementary sequences.

Preferably, a probe for the species *Klebsiella pneumoniae* has a nucleotide sequence which consists of or which comprises a sequence chosen from SEQ ID NO: 34, SEQ ID NO: 38, SEQ ID NO: 39, SEQ ID NO: 44, SEQ ID NO: 47 and their complementary sequences;

a method for the determination of the presence or absence of *Escherichia coli*, according to which a probe is used chosen from those comprising a nucleotide sequence of at least 12 consecutive nucleotide units which is included in one of the sequences chosen from:

SEQ ID NO: 12 and containing at least 5 consecutive nucleotide units included in SEQ ID NO: 61, SEQ ID NO: 26 and containing at least 5 consecutive nucleotide units included in SEQ ID NO: 74, and their complementary sequences.

Preferably, a probe for the species *Escherichia coli* has a nucleotide sequence which consists of or which comprises a sequence chosen from SEQ ID NO: 36, SEQ ID NO: 50 and their complementary sequences.

According to a particular embodiment of these methods, the selected probes are used in combination with a genus probe of the invention.

A further subject of the invention is a nucleotide primer which can be used for the synthesis of a nucleic acid in the presence of a polymerase in a manner known per se, and in particular in amplification methods employing such a synthesis in the presence of a polymerase (PCR, RT-PCR, and the like), said primer comprising an oligonucleotide as defined above. In particular, a primer of the invention may be used for the specific reverse transcription of a messenger RNA sequence of at least one species or at least one group of species of enterobacteria, to obtain a corresponding complementary DNA sequence. Such a reverse transcription may constitute the first stage of an RT-PCR, the next stage being the amplification by PCR of the complementary DNA obtained. The primers of the invention may also be used for the specific amplification by a polymerization chain reaction of the DNA sequence of the rpoB gene of at least one species or at least one group of species of enterobacterium.

According to a special case, said primer comprising an oligonucleotide of the invention comprises, in addition, the sense or antisense sequence of a promoter which is recognized by an RNA polymerase (for example T7, T3, SP6) : such primers can be used in methods for the amplification of nucleic acid that involve a step of transcription, such as, for example, the NASBA or 3SR techniques.

Lastly, a final subject of the invention is a therapeutic probe for treating the infections caused by at least one species or group of species of enterobacterium, said probe comprising an oligonucleotide as defined above. This therapeutic probe, capable of hybridizing with the messenger RNA and/or with the genomic DNA of said bacteria, can block the phenomena of translation and/or transcription and/or replication. The principle of the methods of gene therapy is known and is based, in particular, on the use of a probe corresponding to an antisense strand: the formation of a hybrid between the probe and the sense strand is capable of interfering with at least one of the steps of decoding of the genetic information. Therapeutic probes can hence be used as antibacterial drugs, enabling the infections caused by enterobacteria to be combatted.

DESCRIPTION OF PREFERRED EMBODIMENTS

Under conditions which are specified in Example 1 below, the nucleotide sequence of the DNA corresponding to the rpoB gene of two species of enterobacterium, and also of a species belonging to a family of likewise Gramx negative bacteria, has been determined. This study concerned the species *Escherichia coli, Shigella dysenteriae* and *Pseudomonas putida.*

Regions which are strongly conserved for the enterobacterial species alone, enabling them to be distinguished from the other bacterial genera, were tested for. A useful region of 512 bases, namely from positions 1498 to 2009 of the rpoB gene, expressed with reference to the numbering of the nucleotide sequence of the rpoB gene of *Escherichia coli* ATCC 25290, was thus selected. The sequences of these same regions for other species of enterobacteria, and also for several species not belonging to the family of enterobacteria, were determined.

BRIEF DESCRIPTION OF THE DRAWINGS

The results of these different sequencings are summarized in attached FIGS. 1 to 9, in which the * sign represents a vacant site, representation of which is necessary for the alignment of the sequences, taking account of certain species possessing an additional nucleotide unit at this site.

The results of these investigations, that is to say the alignments of sequences appearing in FIGS. 1 to 9, made it possible to design probes in the regions which are conserved in all species of enterobacteria, which enable the presence or absence of at least one bacterium of any kind belonging to the family of enterobacteria to be detected. In addition, the use of probes containing mutated regions for one particular species (relative to the reference species, in this case *E. coli*), makes it possible to detect such a species directly. In the sandwich hybridization techniques, using two probes in combination (capture probe and detection probe), a probe specific for the family of enterobacteria and a probe specific for the species in question will, for example, be used in combination. Two probes specific for said species, when they exist, may also be used in combination, these two probes being complementary to nonoverlapping regions of the rpoB gene.

As mentioned above, the nucleotide probes of the invention may be used in the traditional hybridization methods. The nucleic acid to be detected (target) can be DNA or RNA (either of them possibly obtained after amplification). In the case of a double-stranded nucleic acid target, the latter should be denatured before the detection method is carried out. The target nucleic acid may be obtained by extraction, according to known methods, of the nucleic acids from a sample to be examined. The denaturation of a double-stranded nucleic acid may be performed by the known methods of chemical, physical or enzymatic denaturation, and especially by heating to a suitable temperature above 80° C.

In some cases, the demonstration of the presence of a given species of enterobacterium necessitates the use of probes permitting the detection of a point mutation. For this purpose, the procedure should be carried out with probes of a predetermined length (number of nucleotide units), under conditions which are themselves predetermined.

Further details are given below, reference being made more especially to the sandwich hybridization method which constitutes one of the most convenient hybridization methods at the present time. This method entails bringing a first probe, bound to a solid support, into contact with a solution containing the nucleic acid to be analyzed, and bringing said support into contact with the detection probe, incubation of the mixture obtained, rinsing of the support to remove the constituents which are not bound to the support by specific hybridization, and the qualitative or quantitative detection, using a reaction for visualization of the label bound to the support, of the bound detection probe. The visualization of the presence of the label may be performed, for example, by colorimetry, fluorescence or luminescence.

The bringing of the capture probe into contact with the sample and with the detection probe may be performed sequentially, where appropriate with intermediate rinsing of the support. The procedure may also be carried out by bringing the capture probe, bound to the support, into contact simultaneously or virtually simultaneously with a solution containing the sample and the detection probe, which probes may be added in mixture form or separately.

The stages of incubation and of consecutive washing, which constitute the key steps of the sandwich hybridization method, are each performed at a constant temperature which can, for example, lie within the range mentioned above (see the "Definitions"). Nucleic acid hybrids are known to have a dissociation temperature which depends on the number of bases hybridized (the temperature increasing with the size of the hybrid), and which also depends on the nature of the bases hybridized and, for each base hybridized, on the nature of the adjacent bases. Dissociation of the hybrids takes place over a temperature span of a few degrees, and may be readily determined, for example in UV spectroscopy. It is possible to determine experimentally the half-dissociation temperature of the hybrid formed by a given probe with the target of complementary sequence by simple routine experiments The hybridization temperature used in the sandwich hybridization technique must clearly be chosen to be below the half-dissociation temperature. More precisely, the procedure is performed at a temperature below the half-dissociation temperature of the less stable hybrid of the two hybrids formed by the target with, on the one hand the capture probe, and on the other hand the detection probe, so that both hybrids are stable at the temperature at which the procedure is performed. A point mutation, that is to say a mutation giving rise to a mispairing affecting a single base pair in the hybrid, gives rise to a modification, generally a lowering, of the half-dissociation temperature. Using sufficiently short probes, a single mispairing of this kind may give rise to a relatively large lowering of the half-dissociation temperature, of the order of a few degrees. Thus, by choosing, with the aid of preliminary routine experiments, a probe of suitable length, working in a given buffer solution, it is possible to determine a temperature at which it will be possible to observe hybridization only in the case where the probe is strictly complementary to the target. In addition, by means of the choice of short probes of predetermined length, it is possible to carry out the sandwich hybridization technique at a predetermined single temperature, for example 37° C. For a more detailed discussion of the sandwich hybridization technique with the use of short probes, reference may be made, in particular, to Patent Application FR-2,663,040.

The examples which follow illustrate the invention.

EXAMPLE 1

Conserved primers were selected in order to amplify the sequenced portion:

CM7: 5' AACCAGTTCCGCGTTGGCCTGG 1348–1405
CM31 5' CCTGAACAACACGCTCGGA 2473–2455 the coordinates being expressed according to the coding sequence of the rpoB gene of *E. coli* Genbank V00340.

The target DNA is extracted from each bacterium according to the following technique. 1.5 ml of bacterial culture is centrifuged and the pellet taken up in 75µl of Tris buffer (25 mM Tris, 10 mM EDTA, 50 mM sucrose, pH 8) and 25µl of lysozyme solution (1 mg/ml in Tris buffer). After incubation for 30 min at 37° C., 50 µl of phenol are added and the tube is shaken vigorously for 30 seconds. 50µl of chloroform are added and the tube is shaken again for 2 seconds. After centrifugation for 5 min, the aqueous phase is recovered.

The DNA is amplified according to the PCR technique of Saiki et al. (Saiki et al., 1988, Science 239, 487–494) using a Perkin-Elmer PCR 480 apparatus. The reaction medium (100µl) consists of Tris-HCl 10 mmol/1; $MgCl_2$ 1.5 mmol/1; KCl 50 mmol/1; gelatin 1 mg/ml; DATP, dCTP, dGTP, dTTP 0.5 mmol/1 each; pH 8.3; oligonucleotide CM7, 25 pmol; oligonucleotide CM31, 25 pmol and 10µl of the bacterial DNA preparation. After denaturation for 5 min followed by a centrifugation, the enzyme is added at a concentration of 1.5 U/reaction. PCR is performed over 30 cycles with the parameters 96° C./60° C./74°C. for 1 min, 1 min and 0.7 min, respectively.

The amplified DNA is analyzed by electrophoresis on 0.8% agarose gel in TBE buffer (89 mM Tris base, 89 mM boric acid, 2 mM EDTA). The bands are visualized with ethidium bromide.

The sequence of the fragments thus amplified was established according to standard techniques.

EXAMPLE 2

Use of a specific probe directed against the rpoB gene for the identification of *Escherichia coli*

The probe beginning at nucleotide No. 4 and ending at nucleotide No. 27 of the sequence SEQ ID NO: 12, which is, in principle, specific for *E. coli* strains, was deduced from the alignments of the nucleotide sequences of the rpoB genes in FIG. 4. A collection of bacterial strains was tested by hybridization with the fragment amplified from rpoB, and the results obtained enabled the specificity of this probe to be established.

The hybridization of the PCR product from a target bacterium was performed according to the nonradioactive and semiautomated detection method described in French Patent No. 90/07249. A capture probe S8L corresponding to a probe of eubacterial specificity (described in Patent Application FR No. 93/02127) and an oligonucleotide (corresponding to the specific probe defined above)—enzyme specific detection conjugate are used. The manipulation was performed according to the following protocol.

A 1 ng/ml solution of the capture oligonucleotide in 3 PBS (0.45M NaCl, 0.15M sodium phosphate, pH 7.0), the 5' end of which has reacted with the reagent Aminolink 2 (Applied Biosystems, Foster city, Calif.), is introduced into a microtitration plate (Nunc 439454). The plate is incubated for 2 h at 37° C. and then washed 3 times with 300µl of PBST (1 PBS, 0.05% Tween 20 (Merck 822184)). The reagent Aminolink 2 enables an arm containing a 6-aminohexyl group to be added at the 5' end of the probe. The probe thus coupled to a ligand possessing a polar (primary amine) group, and bound passively to the support, procures an improved signal; see Patent Application FR 91 09057.

The target consisting of 4µl of the amplified product is mixed with 76µl of "salmon-PBS" buffer (3 PBS+salmon sperm DNA 10 µg/ml (Sigma D9156)) and 10µl of 2N sodium hydroxide. The mixture is neutralized 5 min later by adding 10 µl of 2N acetic acid. The mixture is added into the well, in addition to 50 µl of a solution of the oligonucleotide-peroxidase conjugate at a concentration of 0.1 ng/ml with respect to the oligonucleotide in a "horse-PBS" buffer (3 PBS+10% horse serum (Bio Mérieux 55842)). The oligonucleotide-peroxidase conjugate constitutes the detection probe. The plate is incubated for 1 h at 37° C. and washed with 3 300µl of PBST. Into each well are added 100µl of OPD (ortho-phenylenediamine, Cambridge Medical Biotechnology ref/456) substrate in a suitable buffer (0.055M citric acid, 0.1M $Na_2HPO_4$, pH 4.93) at a concentration of 4 mg/ml, to which 30-volumes $H_2O_2$ diluted to 1/1000 is added at the time of reaction. After 20 min of reaction, the enzyme activity is blocked with 100µl of 1N $H_2SO_4$ and reading is performed on an Axia Microreader (Bio Mérieux) at 492 nm.

The target bacteria were, in particular, the following:

22 *E. coli* isolates or strains (including ATCC 25290, 25922, 27165, 10536);

various other Escherichia species (18 isolates): *E. fergusonii*, *E. hermanii*, *E. vulneris*;

8 Shigella species: *S. boydii*, *S. dysenteriae* (including ATCC 29027), *S. flexneri*, *S. sonnei*;

5 Salmonella species: *S. arizonae* (ATCC 13314), *S. choleraesuis* (ATCC 13312), *S. gallinarum*, *S. typhimnrium* (ATCC 14028), *S. spp* (ATCC 9712);

7 diverse enterobacteria: *Citrobacter amalonaticus* (ATCC 25405), *Enterobacter cloacae* (ATCC 13047), *Klebsiella oxytoca*, *K. pneumoniae*, *Kluivera ascorbata*, *Proteus mirabilis*, *Serratia marcescens* (ATCC 8195);

*Pseudomonas aeruginosa* ATCC 35422, *Pseudomonas putida*;

*Enterococcus faecalis*.

The results obtained indicate that the probe combination used is, on subsequent evaluation, specific for *E. coli*. It does not display cross-reactions with the PCR product of the other bacterial species.

Adaptation of the specific combination to the VIDAS (registered trade mark—marketed by the company Bio Mérieux-VITEK) automated apparatus was performed. The wall of the microplate well is in this case replaced by the SPR (trade mark) ("Solid Phase Receptacle"), which is a conical support made from a material sold under the name K resin (butadiene-styrene copolymer) and marketed by the company Bio Mérieux-VITEK (USA). The various reactants are arranged in a multicuvette strip, and the different steps take place in the SPR which is capable of drawing up and expelling the reactants and which hence acts as a pipette. The sandwich hybridization reaction described in the protocol below proceeds on the inner wall of the cone.

The capture oligonucleotide containing at its 5' end the ligand Aminolink 2 (Applied Biosystems—ref. 400808) at a concentration of 1 ng/µl in a volume of 315µl of 4 PBS solution (200 mM sodium phosphate, pH 7.0, 600 mM NaCl) is bound passively to the inner surface of the SPR. After one night at room temperature or two hours at 37° C., the cones are washed twice with PBS-Tween solution and then dried under vacuum. The strip contains, in cuvettes, the reactants needed for the detection, that is to say 200µl of a 0.1 ng/µl solution of the oligonucleotide-alkaline phosphatase detection conjugate, 2 times 600µl of PBS-Tween washing solution and a cuvette of substrate.

10µl of PCR product, in the same buffer as for the microplate protocol above, are introduced into the first well of the strip.

After incubation of the cone for 30 minutes with the PCR target plus detection probe mixture, the cone is washed twice with PBS-Tween solution. 250µl of MUP (4-methylumbelliferyl phosphate) substrate dissolved in diethanolamine buffer are drawn into the cone and then released into a reading cuvette. The apparatus measures the fluorescent signal expressed in RFU (relative fluorescence units) from the cuvette.

The results obtained with this system are the same as those obtained in microplates.

What is claimed is:

1. An oligonucleotide selected from the group consisting of oligonucleotides comprising a first sequence of at least 12 consecutive nucleotide units which is included in at least one of SEQ ID NO: 1 through SEQ ID NO: 52, and oligonucleotides complementary thereto, excluding oligonucleotides having a second sequence selected from the group consisting of SEQ ID NO: 77, SEQ ID NO: 78 and SEQ ID NO: 79.

2. The oligonucleotide as claimed in claim 1, which comprises a nucleotide sequence of at least 12 consecutive nucleotide units which is included in at least one of SEQ ID NO: 1 through SEQ ID NO: 4.

3. The oligonucleotide as claimed in claim 1, which comprises a nucleotide sequence of at least 12 consecutive nucleotide units which is included in at least one of:

SEQ ID NO: 5 and comprises at least 5 consecutive nucleotide units included in SEQ ID NO: 53, SEQ ID NO: 6 and comprises at least 5 consecutive nucleotide units included in SEQ ID NO: 54, SEQ ID NO: 7 and comprises at least 5 consecutive nucleotide units included in SEQ ID NO: 55, SEQ ID NO: 8 and comprises at least 5 consecutive nucleotide units included in SEQ ID NO: 56, SEQ ID NO: 8 and comprises at least 5 consecutive nucleotide units included in SEQ ID NO: 57, SEQ ID NO: 9 and comprises at least 5 consecutive nucleotide units included in SEQ ID NO: 58, SEQ ID NO: 10 and comprises at least 5 consecutive nucleotide units included in SEQ ID NO: 59, SEQ ID NO: 11 and comprises at least 5 consecutive nucleotide units included in SEQ ID NO: 60, SEQ ID NO: 12 and comprises at least 5 consecutive nucleotide units included in SEQ ID NO: 61, SEQ ID NO: 13 and comprises at least 5 consecutive nucleotide units included in SEQ ID NO: 62, SEQ ID NO: 14 and comprises at least 5 consecutive nucleotide units included in SEQ ID NO: 63, SEQ ID NO: 15 and comprises at least 5 consecutive nucleotide units included in SEQ ID NO: 64, SEQ ID NO: 16 and comprises at least 5 consecutive nucleotide units included in SEQ ID NO: 65, SEQ ID NO: 17 and comprises at least 5 consecutive nucleotide units included in SEQ ID NO: 64, SEQ ID NO: 18 and comprises at least 5 consecutive nucleotide units included in SEQ ID NO: 66, SEQ ID NO: 19 and comprises at least 5 consecutive nucleotide units included in SEQ ID NO: 67, SEQ ID NO: 20 and comprises at least 5 consecutive nucleotide units included in SEQ ID NO: 68, SEQ ID NO: 21 and comprises at least 5 consecutive nucleotide units included in SEQ ID NO: 69, SEQ ID NO: 22 and comprises at least 5 consecutive nucleotide units included in SEQ ID NO: 70, SEQ ID NO: 23 and comprises at least 5 consecutive nucleotide units included in SEQ ID NO: 71, SEQ ID NO: 24 and comprises at least 5 consecutive nucleotide units included in SEQ ID NO: 72, SEQ ID NO: 25 and comprises at least 5 consecutive nucleotide units included in SEQ ID NO: 73, SEQ ID NO: 26 and comprises at least 5 consecutive nucleotide units included in SEQ ID NO: 74, SEQ ID NO: 27 and comprises at least 5 consecutive nucleotide units included in SEQ ID NO: 75, and SEQ ID NO: 28 and comprises at least 5 consecutive nucleotide units included in SEQ ID NO: 76.

4. The oligonucleotide as claimed in claim 3, which comprises a nucleotide sequence selected from the group consisting of SEQ ID NO: 29 through SEQ ID NO: 52.

5. The oligonucleotide as claimed in claim 3, which consists of a nucleotide sequence selected from the group consisting of SEQ ID NO: 29 through SEQ ID NO: 52.

6. A probe for the detection, in a biological sample, of bacteria belonging to the family of enterobacteria, said probe comprising an oligonucleotide as claimed in claim 1.

7. The probe as claimed in claim 6, which is immobilized on a solid support.

8. The probe as claimed in claim 6, which is labeled with a tracing agent.

9. A method for detecting whether at least one bacterium belonging to the family of enterobacteria is present in a biological sample, said method comprising:

contacting said biological sample with at least one oligonucleotide as claimed in claim 1, and detecting whether said at least one bacterium is present in said biological sample by determining whether said oligonucleotide probe is hybridized to a nucleic acid of said at least one bacterium.

10. A method for detecting whether at least one bacterium belonging to the family of enterobacteria is present in a biological sample, said method comprising:

contacting said biological sample with at least one oligonucleotide probe selected from the group consisting of oligonucleotides having a sequence of at least 12 consecutive nucleotide units which is included in at least one of SEQ ID NO: 1 through SEQ ID NO: 52, and oligonucleotides complementary thereto, and detecting whether said at least one bacterium is present in said biological sample by determining whether said at least one oligonucleotide probe is hybridized to a nucleic acid of said at least one bacterium.

11. The method as claimed in claim 10, wherein said at least one oligonucleotide probe comprises a nucleotide sequence of at least 12 consecutive nucleotide units which is included in at least one of SEQ ID NO: 1 through SEQ ID NO: 4, and their complementary sequences.

12. The method as claimed in claim 11, wherein said at least one oligonucleotide probe comprises a nucleotide sequence of at least 12 consecutive nucleotide units which is included in at least one of:

SEQ ID NO: 5 and comprises at least 5 consecutive nucleotide units included in SEQ ID NO: 53,
SEQ ID NO: 6 and comprises at least 5 consecutive nucleotide units included in SEQ ID NO: 54,
SEQ ID NO: 7 and comprises at least 5 consecutive nucleotide units included in SEQ ID NO: 55,
SEQ ID NO: 8 and comprises at least 5 consecutive nucleotide units included in SEQ ID NO: 56,
SEQ ID NO: 8 and comprises at least 5 consecutive nucleotide units included in SEQ ID NO: 57,
SEQ ID NO: 9 and comprises at least 5 consecutive nucleotide units included in SEQ ID NO: 58,
SEQ ID NO: 10 and comprises at least 5 consecutive nucleotide units included in SEQ ID NO: 59,
SEQ ID NO: 11 and comprises at least 5 consecutive nucleotide units included in SEQ ID NO: 60,
SEQ ID NO: 12 and comprises at least 5 consecutive nucleotide units included in SEQ ID NO: 61,
SEQ ID NO: 13 and comprises at least 5 consecutive nucleotide units included in SEQ ID NO: 62,
SEQ ID NO: 14 and comprises at least 5 consecutive nucleotide units included in SEQ ID NO: 63,
SEQ ID NO: 15 and comprises at least 5 consecutive nucleotide units included in SEQ ID NO: 64,
SEQ ID NO: 16 and comprises at least 5 consecutive nucleotide units included in SEQ ID NO: 65,
SEQ ID NO: 17 and comprises at least 5 consecutive nucleotide units included in SEQ ID NO: 64,
SEQ ID NO: 18 and comprises at least 5 consecutive nucleotide units included in SEQ ID NO: 66,
SEQ ID NO: 19 and comprises at least 5 consecutive nucleotide units included in SEQ ID NO: 67,
SEQ ID NO: 20 and comprises at least 5 consecutive nucleotide units included in SEQ ID NO: 68,
SEQ ID NO: 21 and comprises at least 5 consecutive nucleotide units included in SEQ ID NO: 69,
SEQ ID NO: 22 and comprises at least 5 consecutive nucleotide units included in SEQ ID NO: 70,
SEQ ID NO: 23 and comprises at least 5 consecutive nucleotide units included in SEQ ID NO: 71,
SEQ ID NO: 24 and comprises at least 5 consecutive nucleotide units included in SEQ ID NO: 72,
SEQ ID NO: 25 and comprises at least 5 consecutive nucleotide units included in SEQ ID NO: 73,
SEQ ID NO: 26 and comprises at least 5 consecutive nucleotide units included in SEQ ID NO: 74,
SEQ ID NO: 27 and comprises at least 5 consecutive nucleotide units included in SEQ ID NO: 75,
SEQ ID NO: 28 and comprises at least 5 consecutive nucleotide units included in SEQ ID NO: 76, and sequences complementary thereto.

13. The method as claimed in claim 12, wherein said at least one oligonucleotide probe comprises a nucleotide sequence selected from the group consisting of SEQ ID NO: 29 through SEQ ID NO: 52.

14. The method as claimed in claim 10, wherein said biological sample is contacted with:

a first oligonucleotide probe comprising a nucleotide sequence of at least 12 consecutive nucleotide units which is included in at least one of SEQ ID NO: 1 through SEQ ID NO: 4, and their complementary sequences, and a second oligonucleotide probe comprising a nucleotide sequence of at least 12 consecutive nucleotide units which is included in at least one of:

SEQ ID NO: 5 and comprises at least 5 consecutive nucleotide units included in SEQ ID NO: 53,
SEQ ID NO: 6 and comprises at least 5 consecutive nucleotide units included in SEQ ID NO: 54,
SEQ ID NO: 7 and comprises at least 5 consecutive nucleotide units included in SEQ ID NO: 55,
SEQ ID NO: 8 and comprises at least 5 consecutive nucleotide units included in SEQ ID NO: 56,
SEQ ID NO: 8 and comprises at least 5 consecutive nucleotide units included in SEQ ID NO: 57,
SEQ ID NO: 9 and comprises at least 5 consecutive nucleotide units included in SEQ ID NO: 58,
SEQ ID NO: 10 and comprises at least 5 consecutive nucleotide units included in SEQ ID NO: 59,
SEQ ID NO: 11 and comprises at least 5 consecutive nucleotide units included in SEQ ID NO: 60,
SEQ ID NO: 12 and comprises at least 5 consecutive nucleotide units included in SEQ ID NO: 61,
SEQ ID NO: 13 and comprises at least 5 consecutive nucleotide units included in SEQ ID NO: 62,
SEQ ID NO: 14 and comprises at least 5 consecutive nucleotide units included in SEQ ID NO: 63,
SEQ ID NO: 15 and comprises at least 5 consecutive nucleotide units included in SEQ ID NO: 64,
SEQ ID NO: 16 and comprises at least 5 consecutive nucleotide units included in SEQ ID NO: 65,
SEQ ID NO: 17 and comprises at least 5 consecutive nucleotide units included in SEQ ID NO: 64,
SEQ ID NO: 18 and comprises at least 5 consecutive nucleotide units included in SEQ ID NO: 66,
SEQ ID NO: 19 and comprises at least 5 consecutive nucleotide units included in SEQ ID NO: 67,
SEQ ID NO: 20 and comprises at least 5 consecutive nucleotide units included in SEQ ID NO: 68,
SEQ ID NO: 21 and comprises at least 5 consecutive nucleotide units included in SEQ ID NO: 69,
SEQ ID NO: 22 and comprises at least 5 consecutive nucleotide units included in SEQ ID NO: 70,
SEQ ID NO: 23 and comprises at least 5 consecutive nucleotide units included in SEQ ID NO: 71,
SEQ ID NO: 24 and comprises at least 5 consecutive nucleotide units included in SEQ ID NO: 72,
SEQ ID NO: 25 and comprises at least 5 consecutive nucleotide units included in SEQ ID NO: 73,
SEQ ID NO: 26 and comprises at least 5 consecutive nucleotide units included in SEQ ID NO: 74,
SEQ ID NO: 27 and comprises at least 5 consecutive nucleotide units included in SEQ ID NO: 75,
SEQ ID NO: 28 and comprises at least 5 consecutive nucleotide units included in SEQ ID NO: 76, and sequences complementary thereto, and wherein said first and second oligonucleotide probes hybridize with nonoverlapping regions of a nucleic acid corresponding to an rpoB gene of enterobacteria.

15. The method as claimed in claim 10, wherein the method is for detecting whether Salmonella sofia is present in a biological sample, and wherein said probe comprises a nucleotide sequence of at least 12 consecutive nucleotide units which is included in at least one of:

SEQ ID NO: 5 and comprises at least 5 consecutive nucleotide units included in SEQ ID NO: 53, SEQ ID NO: 27 and comprises at least 5 consecutive nucleotide units included in SEQ ID NO: 75, and their complementary sequences.

16. The method as claimed in claim 15, wherein said oligonucleotide probe has a nucleotide sequence which comprises a sequence selected from the group consisting of SEQ ID NO: 29, SEQ ID NO: 51 and their complementary sequences.

17. The method as claimed in claim 10, wherein the method is for detecting whether Salmonella typhimurium is present in a biological sample, and wherein said oligonucleotide probe comprises a nucleotide sequence of at least 12 consecutive nucleotide units which is included in at least one of:

SEQ ID NO: 6 and comprises at least 5 consecutive nucleotide units included in SEQ ID NO: 54, SEQ ID NO: 11 and comprises least 5 consecutive nucleotide units included in SEQ ID NO: 60, SEQ ID NO: 24 and comprises at least 5 consecutive nucleotide units included in SEQ ID NO: 72, SEQ ID NO: 25 and comprises at least 5 consecutive nucleotide units included in SEQ ID NO: 73, and their complementary sequences.

18. The method as claimed in claim 17, wherein the oligonucleotide probe has a nucleotide sequence which comprises a sequence selected from the group consisting of SEQ ID NO: 30, SEQ ID NO: 35, SEQ ID NO: 48, SEQ ID NO: 49, SEQ ID NO: 52 and their complementary sequences.

19. The method as claimed in claim 10, wherein the method is for detecting whether Shigella dysenteriae is present in a biological sample, and wherein said oligonucleotide probe comprises a nucleotide sequence of at least 12 consecutive nucleotide units which is included in SEQ ID NO: 7 and comprises at least 5 consecutive nucleotide units included in SEQ ID NO: 55 and its complementary sequence.

20. The method as claimed in claim 19, wherein the oligonucleotide probe has a nucleotide sequence which comprises a sequence selected from the group consisting of SEQ ID NO: 31 and its complementary sequence.

21. The method as claimed in claim 10, wherein the method is for detecting whether Escherichia fergussoni is present in a biological sample, and wherein said oligonucleotide probe comprises a nucleotide sequence of at least 12 consecutive nucleotide units which is included in at least one of:

SEQ ID NO: 8 and comprises at least 5 consecutive nucleotide units included in SEQ ID NO: 56, SEQ ID NO: 8 and comprises at least 5 consecutive nucleotide units included in SEQ ID NO: 57, SEQ ID NO: 19 and comprises at least 5 consecutive nucleotide units included in SEQ ID NO: 67, and their complementary sequences.

22. The method as claimed in claim 21, wherein the oligonucleotide probe has a nucleotide sequence which comprises a sequence selected from the group consisting of SEQ ID NO: 32, SEQ ID NO: 43 and their complementary sequences.

23. The method as claimed in claim 10, wherein the method is for detecting whether Enterobacter cloacae is present in a biological sample, and wherein said oligonucleotide probe comprises a nucleotide sequence of at least 12 consecutive nucleotide units which is included in at least one of:

SEQ ID NO: 9 and comprises at least 5 consecutive nucleotide units included in SEQ ID NO: 58, SEQ ID NO: 13 and comprises at least 5 consecutive nucleotide units included in SEQ ID NO: 62, SEQ ID NO: 16 and comprises at least 5 consecutive nucleotide units included in SEQ ID NO: 65, SEQ ID NO: 17 and comprises at least 5 consecutive nucleotide units included in SEQ ID NO: 64, SEQ ID NO: 18 and comprises at least 5 consecutive nucleotide units included in SEQ ID NO: 66, SEQ ID NO: 21 and comprises at least 5 consecutive nucleotide units included in SEQ ID NO: 69, SEQ ID NO: 22 and comprises at least 5 consecutive nucleotide units included in SEQ ID NO: 70, and their complementary sequences.

24. The method as claimed in claim 23, wherein the oligonucleotide probe has a nucleotide sequence which comprises a sequence selected from the group consisting of SEQ ID NO: 33, SEQ ID NO: 37, SEQ ID NO: 40, SEQ ID NO: 41, SEQ ID NO: 42, SEQ ID NO: 45, SEQ ID NO: 46 and their complementary sequences.

25. The method as claimed in claim 10, wherein the method is for detecting whether Klebsiella pneumoniae is present in a biological sample, and wherein said oligonucleotide probe comprises a nucleotide sequence of at least 12 consecutive nucleotide units which is included in at least one of:

SEQ ID NO: 10 and comprises at least 5 consecutive nucleotide units included in SEQ ID NO: 59, SEQ ID NO: 14 and comprises at least 5 consecutive nucleotide units included in SEQ ID NO: 63, SEQ ID NO: 15 and comprises at least 5 consecutive nucleotide units included in SEQ ID NO: 64, SEQ ID NO: 20 and comprises at least 5 consecutive nucleotide units included in SEQ ID NO: 68, SEQ ID NO: 23 and comprises at least 5 consecutive nucleotide units included in SEQ ID NO: 71, and their complementary sequences.

26. The method as claimed in claim 25, wherein the oligonucleotide probe has a nucleotide sequence which comprises a sequence selected from the group consisting of SEQ ID NO: 34, SEQ ID NO: 38, SEQ ID NO: 39, SEQ ID NO: 44, SEQ ID NO: 47 and their complementary sequences.

27. The method as claimed in claim 10, wherein the method is for detecting whether Escherichia coli is present in a biological sample, and wherein said oligonucleotide probe comprises a nucleotide sequence of at least 12 consecutive nucleotide units which is included in at least one of:

SEQ ID NO: 12 and comprises at least 5 consecutive nucleotide units included in SEQ ID NO: 61, SEQ ID NO: 26 and comprises at least 5 consecutive nucleotide units included in SEQ ID NO: 74, and their complementary sequences.

28. The method as claimed in claim 27, wherein the oligonucleotide probe has a nucleotide sequence which comprises a sequence selected from the group consisting of SEQ ID NO: 36, SEQ ID NO: 50 and their complementary sequences.

29. The oligonucleotide as claimed in claim 1, which is a nucleotide primer for the synthesis of a nucleic acid in the presence of a polymerase.

30. A method of synthesizing a nucleic acid, comprising hybridizing the oligonucleotide according to claim 29 to a nucleotide.

31. The oligonucleotide as claimed in claim 1, which is a therapeutic probe.

32. A method of treating a condition associated with enterobacteria, said method comprising hybridizing the oligonucleotide according to claim 31 to a nucleic acid of said enterobacteria.

* * * * *

UNITED STATES PATENT AND TRADEMARK OFFICE
CERTIFICATE OF CORRECTION

PATENT NO. : 5,786,147
DATED : July 28, 1998
INVENTOR(S) : Claude MABILAT and Raoult DIDIER It is certified that error appears in the above-identified patent and that said Letters Patent is hereby corrected as shown below:

On the title page, item [30], the priority data should read

--Sep. 18, 1995 [FR] France ........ 95 11125--.

Signed and Sealed this

Nineteenth Day of January, 1999

Attest:

Attesting Officer

*Acting Commissioner of Patents and Trademarks*

UNITED STATES PATENT AND TRADEMARK OFFICE
CERTIFICATE OF CORRECTION

PATENT NO. : 5,786,147
DATED : July 28, 1998
INVENTOR(S) : Claude Mabilat and Didier Raoult It is certified that error appears in the above-identified patent and that said Letters Patent is hereby corrected as shown below:

On the title page, under item [75], information for the second inventor should be changed from "Raoult Didier, Marseilles" to --Didier Raoult, Marseille--.

under item [73] Assignees: should read -- Bio Merieux, Marcy l'Etoile, France and Universite De La Mediterranee AIX Marseille, Marseille Cedex, France --.

Signed and Sealed this

Seventeenth Day of August, 1999

Attest:

Q. TODD DICKINSON

*Attesting Officer*   Acting Commissioner of Patents and Trademarks

SEQUENCE LISTING ( 1 ) GENERAL INFORMATION:

( i i i ) NUMBER OF SEQUENCES: 79

( 2 ) INFORMATION FOR SEQ ID NO:1:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GCAGTGAAAG AGTTCTT        17

( 2 ) INFORMATION FOR SEQ ID NO:2:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

CAGGCTTCGA AGTTCGAGAA CGTACACCCG A        31

( 2 ) INFORMATION FOR SEQ ID NO:3:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

TACCTGTCTG CTATYGAAGA AGGCAACTAC GTTATCGC        38

( 2 ) INFORMATION FOR SEQ ID NO:4:

( i ) SEQUENCE CHARACTERISTICS:
        ( A ) LENGTH: 102 base pairs ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:4:

TGCCGTAGCA AAGGCGAATC CAGCTTGTTC AGCCGYGACC AGGTTGACTA CATGGACGTW    60

TCCACCCAGC AGGTGGTMTC CGTCGGTGCG TCCCTGATCC CG    102

( 2 ) INFORMATION FOR SEQ ID NO:5:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:5:

GCGGCAGTGA AAGAGTTCTT    20

( 2 ) INFORMATION FOR SEQ ID NO:6:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:6:

GCCGCAGTGA AAGAGTTCTT    20

( 2 ) INFORMATION FOR SEQ ID NO:7:

( i ) SEQUENCE CHARACTERISTICS:
            ( A ) LENGTH: 34 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:7:

GAACAACCCG CTGTCCGAGA TTACGCACAA ACGT    34

( 2 ) INFORMATION FOR SEQ ID NO:8:

( i ) SEQUENCE CHARACTERISTICS:
            ( A ) LENGTH: 33 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:8:

TCTGAGATTA CACACAAGCG TCGTATCTCC GCA    33

( 2 ) INFORMATION FOR SEQ ID NO:9:

( i ) SEQUENCE CHARACTERISTICS:
            ( A ) LENGTH: 30 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:9:

CAAACGTCGT ATCTCTGCAC TCGGCCCAGG     30

( 2 ) INFORMATION FOR SEQ ID NO:10:

( i ) SEQUENCE CHARACTERISTICS:
      ( A ) LENGTH: 32 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:10:

TCTGACCCGT GAGCGCGCAG GCTTCGAAGT TC     32

( 2 ) INFORMATION FOR SEQ ID NO:11:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:11:

TCTGACCCGC GAACTGGCAG GCTTCGA     27

( 2 ) INFORMATION FOR SEQ ID NO:12:

( i ) SEQUENCE CHARACTERISTICS:
      ( A ) LENGTH: 30 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:12:

GGTCTGATCA ACTCTCTGTC CGTGTACGCA     30

( 2 ) INFORMATION FOR SEQ ID NO:13:

( i ) SEQUENCE CHARACTERISTICS:
      ( A ) LENGTH: 29 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:13:

GTGTACGCAC AGACAAACGA ATACGGCTT     29

( 2 ) INFORMATION FOR SEQ ID NO:14:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:14:

GTCCGTGTAC GCGCAGACCA ACGAATA                                          27

( 2 ) INFORMATION FOR SEQ ID NO:15:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

CGCGCAGACC AACGAATA                                                    18

( 2 ) INFORMATION FOR SEQ ID NO:16:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

CAAACGAATA CGGTTTCCTT GAGAC                                            25

( 2 ) INFORMATION FOR SEQ ID NO:17:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

CCTTGAGACC CCGTA                                                       15

( 2 ) INFORMATION FOR SEQ ID NO:18:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

CGTAAAGTGA CTGACGGTGT TGT                                              23

( 2 ) INFORMATION FOR SEQ ID NO:19:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

CGTAAAGTGA TTGACGGTGT TGT                                              23

( 2 ) INFORMATION FOR SEQ ID NO:20:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:20:

CGTAAAGTGA CCAACGGTGT 20

( 2 ) INFORMATION FOR SEQ ID NO:21:

( i ) SEQUENCE CHARACTERISTICS:
  ( A ) LENGTH: 22 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:21:

CGGTGTTGTT ACCGACGAAA TT 22

( 2 ) INFORMATION FOR SEQ ID NO:22:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:22:

TACCTGTCTG CTATTGAAGA AGGCAACTAC 30

( 2 ) INFORMATION FOR SEQ ID NO:23:

( i ) SEQUENCE CHARACTERISTICS:
  ( A ) LENGTH: 19 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:23:

TGGATGAAAA CGGCCACTT 19

( 2 ) INFORMATION FOR SEQ ID NO:24:

( i ) SEQUENCE CHARACTERISTICS:
  ( A ) LENGTH: 14 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:24:

GTAGAAGATT TGGT 14

( 2 ) INFORMATION FOR SEQ ID NO:25:

( i ) SEQUENCE CHARACTERISTICS:
  ( A ) LENGTH: 22 base pairs
  ( B ) TYPE: nucleic acid
  ( C ) STRANDEDNESS: single
  ( D ) TOPOLOGY: linear (  i  i  ) MOLECULE TYPE: DNA (genomic)

(  x  i  ) SEQUENCE DESCRIPTION: SEQ ID NO:25:

TGGTGACCTG CCGTAGCAAA GG 22

( 2 ) INFORMATION FOR SEQ ID NO:26:

(  i  ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear (  i  i  ) MOLECULE TYPE: DNA (genomic)

(  x  i  ) SEQUENCE DESCRIPTION: SEQ ID NO:26:

CAGGCGAACT CCAACTTGGA TGA 23

( 2 ) INFORMATION FOR SEQ ID NO:27:

(  i  ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear (  i  i  ) MOLECULE TYPE: DNA (genomic)

(  x  i  ) SEQUENCE DESCRIPTION: SEQ ID NO:27:

CAGCTTGTTC AGCCGTGACC AGGTTGACTA 30

( 2 ) INFORMATION FOR SEQ ID NO:28:

(  i  ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear (  i  i  ) MOLECULE TYPE: DNA (genomic)

(  x  i  ) SEQUENCE DESCRIPTION: SEQ ID NO:28:

ACATGGACGT TTCCACCCAG CAGGTGG 27

( 2 ) INFORMATION FOR SEQ ID NO:29:

(  i  ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear (  i  i  ) MOLECULE TYPE: DNA (genomic)

(  x  i  ) SEQUENCE DESCRIPTION: SEQ ID NO:29:

GCGGCAGTGA AAGAG 15

( 2 ) INFORMATION FOR SEQ ID NO:30:

(  i  ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear (  i  i  ) MOLECULE TYPE: DNA (genomic)

(  x  i  ) SEQUENCE DESCRIPTION: SEQ ID NO:30:

GCCGCAGTGA AAGAG 15

( 2 ) INFORMATION FOR SEQ ID NO:31:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

AACCCGCTGT CCGAGATTAC GCA 23

( 2 ) INFORMATION FOR SEQ ID NO:32:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:32:

TACACACAAG CGTCGT 16

( 2 ) INFORMATION FOR SEQ ID NO:33:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:33:

CGTATCTCTG CACTCGG 17

( 2 ) INFORMATION FOR SEQ ID NO:34:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:34:

CGTGAGCGCG CAGGCTTC 18

( 2 ) INFORMATION FOR SEQ ID NO:35:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:35:

CCGCGAACTG GCAGGCTTC 19

( 2 ) INFORMATION FOR SEQ ID NO:36:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:36:

GATCAACTCT CTGTCCGTG                                                                       19

( 2 ) INFORMATION FOR SEQ ID NO:37:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:37:

GCACAGACAA ACGAATAC                                                                         18

( 2 ) INFORMATION FOR SEQ ID NO:38:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:38:

GTGTACGCGC AGACTCAAC                                                                        19

( 2 ) INFORMATION FOR SEQ ID NO:39:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:39:

CGCGCAGACC AACG                                                                             14

( 2 ) INFORMATION FOR SEQ ID NO:40:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:40:

GGAATACGGT TTCCTTG                                                                          17

( 2 ) INFORMATION FOR SEQ ID NO:41:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:41:

CCTTGAGACC CCGTA  15

( 2 ) INFORMATION FOR SEQ ID NO:42:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:42:

CGTAAAGTGA CTGACGG  17

( 2 ) INFORMATION FOR SEQ ID NO:43:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:43:

CGTAAAGTGA TTGACGG  17

( 2 ) INFORMATION FOR SEQ ID NO:44:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:44:

GTAAAGTGAC CAACGGTG  18

( 2 ) INFORMATION FOR SEQ ID NO:45:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:45:

GTGTTGTTAC CGACGAAA  18

( 2 ) INFORMATION FOR SEQ ID NO:46:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:46:

```
GTCTGCTATT GAAGAAGGC                                                                           19
```

(2) INFORMATION FOR SEQ ID NO:47:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:47:

```
TGGATGAAAA CGGCCACTT                                                                           19
```

(2) INFORMATION FOR SEQ ID NO:48:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:48:

```
GTAGAAGATT TGGT                                                                                14
```

(2) INFORMATION FOR SEQ ID NO:49:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:49:

```
TGGTGACCTG CCGTA                                                                               15
```

(2) INFORMATION FOR SEQ ID NO:50:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:50:

```
CGAACTCCAA CTTGGATGA                                                                           19
```

(2) INFORMATION FOR SEQ ID NO:51:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:51:

```
GTTCAGCCGT GACCAGGTTG                                                                          20
```

(2) INFORMATION FOR SEQ ID NO:52:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:52:

GGACGTTTCC ACCCAGC 17

( 2 ) INFORMATION FOR SEQ ID NO:53:

( i ) SEQUENCE CHARACTERISTICS:
        ( A ) LENGTH: 5 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:53:

GGCAG 5

( 2 ) INFORMATION FOR SEQ ID NO:54:

( i ) SEQUENCE CHARACTERISTICS:
        ( A ) LENGTH: 5 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:54:

CGCAG 5

( 2 ) INFORMATION FOR SEQ ID NO:55:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:55:

TGTCCGAGA 9

( 2 ) INFORMATION FOR SEQ ID NO:56:

( i ) SEQUENCE CHARACTERISTICS:
        ( A ) LENGTH: 5 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:56:

ACACA 5

( 2 ) INFORMATION FOR SEQ ID NO:57:

( i ) SEQUENCE CHARACTERISTICS:
        ( A ) LENGTH: 5 base pairs
        ( B ) TYPE: nucleic acid
        ( C ) STRANDEDNESS: single
        ( D ) TOPOLOGY: linear (i i) MOLECULE TYPE: DNA (genomic)

(x i) SEQUENCE DESCRIPTION: SEQ ID NO:57:

GCGTC  5

(2) INFORMATION FOR SEQ ID NO:58:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:58:

TCTCTGCAC  9

(2) INFORMATION FOR SEQ ID NO:59:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:59:

AGCGCGCAG  9

(2) INFORMATION FOR SEQ ID NO:60:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:60:

GAACTGGCAG  10

(2) INFORMATION FOR SEQ ID NO:61:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:61:

ACTCTCTGT  9

(2) INFORMATION FOR SEQ ID NO:62:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:62:

AGACAAACG                                                                                          9

(2) INFORMATION FOR SEQ ID NO:63:

(i) SEQUENCE CHARACTERISTICS:
        (A) LENGTH: 5 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:63:

GCAGA                                                                                              5

(2) INFORMATION FOR SEQ ID NO:64:

(i) SEQUENCE CHARACTERISTICS:
        (A) LENGTH: 5 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:64:

AGACC                                                                                              5

(2) INFORMATION FOR SEQ ID NO:65:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:65:

ACGGTTTCC                                                                                          9

(2) INFORMATION FOR SEQ ID NO:66:

(i) SEQUENCE CHARACTERISTICS:
        (A) LENGTH: 5 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:66:

TGACT                                                                                              5

(2) INFORMATION FOR SEQ ID NO:67:

(i) SEQUENCE CHARACTERISTICS:
        (A) LENGTH: 5 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:67:

TGATT                                                                                              5

(2) INFORMATION FOR SEQ ID NO:68:

( i ) SEQUENCE CHARACTERISTICS:
  ( A ) LENGTH: 5 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:68:

GACCA 5

( 2 ) INFORMATION FOR SEQ ID NO:69:

( i ) SEQUENCE CHARACTERISTICS:
  ( A ) LENGTH: 5 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:69:

TTACC 5

( 2 ) INFORMATION FOR SEQ ID NO:70:

( i ) SEQUENCE CHARACTERISTICS:
  ( A ) LENGTH: 9 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:70:

CTATTGAAG 9

( 2 ) INFORMATION FOR SEQ ID NO:71:

( i ) SEQUENCE CHARACTERISTICS:
  ( A ) LENGTH: 5 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:71:

AAACG 5

( 2 ) INFORMATION FOR SEQ ID NO:72:

( i ) SEQUENCE CHARACTERISTICS:
  ( A ) LENGTH: 8 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:72:

AGATTTGG 8

( 2 ) INFORMATION FOR SEQ ID NO:73:

( i ) SEQUENCE CHARACTERISTICS:
  ( A ) LENGTH: 5 base pairs
  ( B ) TYPE: nucleic acid
  ( C ) STRANDEDNESS: single
  ( D ) TOPOLOGY: linear (i i) MOLECULE TYPE: DNA (genomic)

(x i) SEQUENCE DESCRIPTION: SEQ ID NO:73:

TGACC 5

(2) INFORMATION FOR SEQ ID NO:74:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:74:

CAACTTGGA 9

(2) INFORMATION FOR SEQ ID NO:75:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:75:

GCCGTGACC 9

(2) INFORMATION FOR SEQ ID NO:76:

(i) SEQUENCE CHARACTERISTICS:
        (A) LENGTH: 5 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:76:

TTCCA 5

(2) INFORMATION FOR SEQ ID NO:77:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:77:

CTAGGATCCT TAGAATTCAA CCCGCTGTCC 30

(2) INFORMATION FOR SEQ ID NO:78:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:78:

TACAACTGGC AGGCTGCTTG A 21

(2) INFORMATION FOR SEQ ID NO:79:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:79:

TGTGCCAGCG GTACTGGACA GACCAACGAA AGATTA 36